(12) United States Patent
Bertola et al.

(10) Patent No.: US 6,174,833 B1
(45) Date of Patent: Jan. 16, 2001

(54) PROCESS FOR THE PREPARATION OF IMPROVED VANADIUM-PHOSPHORUS CATALYSTS AND USE THEREOF FOR THE PRODUCTION OF MALEIC ANHYDRIDE

(75) Inventors: Aldo Bertola, Milan; Salvatore Cassarino, Rome, both of (IT); Veron K. Nsunda, Namur (BE)

(73) Assignee: Pantochim S.A., Feluy (BE)

( * ) Notice: Under 35 U.S.C. 154(b), the term of this patent shall be extended for 0 days.

(21) Appl. No.: 09/337,541

(22) Filed: Jun. 22, 1999

(30) Foreign Application Priority Data

Jun. 23, 1998 (BE) .................................................. 09800475

(51) Int. Cl.$^7$ ........................ B01J 27/186; B01J 27/198; C07D 315/00; C07D 307/33
(52) U.S. Cl. ............................................ 502/209; 549/263
(58) Field of Search .............................. 502/209; 549/263

(56) References Cited

U.S. PATENT DOCUMENTS

| | | |
|---|---|---|
| 3,293,268 | 12/1966 | Bergman et al. . |
| 3,864,280 * | 2/1975 | Schneider .............................. 502/209 |
| 4,064,070 | 12/1977 | Harrison . |
| 4,132,670 | 1/1979 | Katsumoto et al. . |
| 4,247,419 | 1/1981 | Vartuli et al. ........................ 252/435 |
| 4,315,864 | 2/1982 | Bremer et al. . |
| 4,317,777 | 3/1982 | Higgins et al. . |
| 4,317,778 * | 3/1982 | Blum et al. ........................... 549/259 |
| 4,333,853 | 6/1982 | Milberger et al. . |
| 4,336,198 | 6/1982 | Dolhyj et al. . |
| 4,392,986 | 7/1983 | Yang et al. . |
| 4,562,268 | 12/1985 | Wrobleski et al. . |
| 4,632,915 | 12/1986 | Keppel et al. . |
| 5,137,860 | 8/1992 | Ebner et al. . |
| 5,847,163 * | 12/1998 | Schneider ............................. 549/233 |

FOREIGN PATENT DOCUMENTS 9529006   11/1995   (WO) .

OTHER PUBLICATIONS

J.W. Johnson et al., "Preparation and Characterization of VO(HPO$_4$)–0.5H$_2$o and Its Topotactic Transformation to (VO)$_2$P$_2$O$_7$", J. Am. Chem. Soc., 106, 8123 (1984).
F. Cavani et al., "The Chemistry of Catalysts Based on Vanadium–Phosphorus Oxides Note IV: Catalytic Behaviour of Catalysts Prepared in Organic Medium in the Oxidation of C$_4$ Fraction", Appl. Catal., 9, 191 (1984).
H.S. Horowitz et al., Appl. Catal., 38, 193 (1988).
R. S. K. Bej et al., Appl. Catal., 83, 149 (1992).
R. Sant et al., J. Catal., 143, 215 (1993).

* cited by examiner

*Primary Examiner*—Alan L. Rotman
*Assistant Examiner*—Rita Desai
(74) *Attorney, Agent, or Firm*—Stevens, Davis, Miller & Mosher, LLP

(57) ABSTRACT

A process for the preparation of oxidation catalysts containing vanadium-phosphorus mixed oxides, consisting of:
  a) contacting a phosphorus compound with a vanadium compound in an organic solvent under conditions allowing the preparation, recovery, drying of said precursor,
  b) submitting the precursor, prior to calcination, to a treatment by contacting with a stream of dry inert gas containing vapors of an aliphatic anhydride, having from 4 to 8 carbon atoms, preferably acetic anhydride, at a temperature not exceeding 200° C.,
  c) calcinating the precursor under an atmosphere containing air, steam, or inert gas or a mixture of them at a temperature between 350° C. and 550° C. at controlled rate of temperature increase during the time necessary to obtain active catalysts,
  d) using of said catalysts for the production of maleic anhydride by oxidation of aliphatic hydrocarbons.

The catalysts prepared according the procedures of this invention are particularly suited for use for the production of maleic anhydride, preferably by partial or total gas recycle process.

31 Claims, No Drawings

US 6,174,833 B1

PROCESS FOR THE PREPARATION OF IMPROVED VANADIUM-PHOSPHORUS CATALYSTS AND USE THEREOF FOR THE PRODUCTION OF MALEIC ANHYDRIDE

This application claims priority under 35 USC §119 from Belgian patent application 09800475 filed Jun. 23, 1998, incorporated herein by reference in its entirety.

FIELD OF THE INVENTION

This invention relates to a method of producing vanadium-phosphorus mixed oxide catalyst for the manufacture of maleic anhydride. More particularly the present invention provides a process for producing mature, active catalysts suitable for commercial production of maleic anhydride by oxidation of aliphatic hydrocarbons, particularly n-butane, in the vapor phase, with a gas containing molecular oxygen, such as air, or oxygen, in a stream of exhaust gas recycled from the reaction effluent, following the recovery of maleic anhydride.

BACKGROUND OF THE INVENTION

Maleic anhydride is a substantial commercial product made throughout the word for over fifty years. It is used alone or in combination with other materials mostly as a precursor for other products, including resins, pharmaceuticals and food additives.

Hundreds of articles and patents have been published related to the vanadium phosphorus oxides catalysts since Bergman et al, U.S. Pat. No. 3,293,268, taught the process of oxidizing saturated aliphatic hydrocarbons to produce maleic anhydride using such catalysts, often referred to as mixed oxides of vanadium and phosphorus. Bulk analysis of the active, mature catalyst shows the catalyst to be generally crystalline vanadyl pyrophosphate. However, as yet there are many factors not clearly understood that are important to the making of active, mature catalysts giving commercially acceptable productivities, yields and lives.

Numerous methods of making the vanadium-phosphorus oxide catalysts with and without promoters are disclosed and taught in the prior art. Generally, such catalysts are made by contacting suitable vanadium compounds under conditions which result in the vanadium being in the +4 valence, and reacted with the phosphorus to form a catalyst precursor consisting essentially of hydrated vanadyl hydrogen phosphate. The catalyst precursor is subsequently recovered by techniques well know in the art, such as drying, filtering and centrifuging, and treated physically and thermally by several conventional practices to form "calcined" mature catalysts.

Very few methods don't use calcination as an integral part of the process of production of an active catalyst. U.S. Pat. No. 4,317,778, for instance, describes a process where the final activation of the catalyst precursor is claimed to occur by introducing the catalyst precursor into water to form an aqueous slurry and by spray drying the slurry to form microspheroidal catalyst particles to be used in fluid bed reactors.

The methods used for the calcination of the catalyst precursor may be divided into two broad categories
1) calcination performed in equipment other than the reactor (external calcination) and
2) calcination in the reactor tubes, under hydrocarbon and air, usually mild operating conditions (in-situ calcination).

An external calcination method which results in a good, competitive catalyst has many advantages over the in-situ procedure. Firstly, productive capacity is lost, usually for weeks, during the in-situ calcination operating at below normal feed concentrations and throughput. Secondly, since the calcination procedure is a very sensitive operation which, if done improperly, results in inferior catalysts, the total reactor charge is put at risk in the in-situ calcination procedure, since the whole catalyst charge is calcined at the same time. The external calcination has the advantage of calcining the catalyst in smaller increments, resulting not only in lower risk of inferior catalyst charged to the commercial reactor, but allowing known procedures for measuring and controlling the quality of the catalyst. Better performance in yield, productivity and life results.

Prior art teaches procedures for both in-situ and external calcination. In both methods the ultimate form of the mature catalyst, in the bulk, is crystalline vanadyl pyrophosphate with various degrees of activity and selectivity for the production of maleic anhydride. Usually in the in-situ method the catalyst in the precursor form is charged to the reactor and brought up to reacting conditions using a feed of hydrocarbon and air. After several days or weeks of producing maleic anhydride at low rate, the precursor is converted to the active vanadyl pyrophosphate with the bulk of the vanadium very close to a valence of +4.

Generally, in the external calcination procedures, the prior art teaches that the catalyst be partially oxidized during the calcination. For reason not totally understood, partial oxidation of vanadium is required to make catalysts with high performance. Vanadium oxidation levels of above 4.0 and below 4.8 are considered favorable. The external calcination procedures described in prior art are varied, using batch and continuous thermal systems. Gaseous atmospheres are controlled in many cases. Gaseous atmospheres containing a combination or mixture of hydrocarbon and oxygen are usually not used, because of the difficulty in controlling the exothermal oxidation.

U.S. Pat. No. 5,137,860 teaches a process for conversion of vanadium-phosphorus catalyst precursors to active catalysts by subjecting the catalyst precursor to elevated temperatures in three stages:
   a) an initial heat-up stage in an atmosphere of air, steam and nitrogen,
   b) a rapid heat-up stage at a programmed heat-up rate in an air/steam atmosphere and
   c) a maintenance-finishing stage, using consecutively an oxygen containing and a non-oxidizing atmosphere.

U.S. Pat. No. 4,562,268 relates to a process for the production of maleic anhydride by oxidation of aliphatic hydrocarbons in the vapor phase using phosphorus-vanadium mixed oxide catalysts. The catalysts employed are normally prepared by introducing pentavalent vanadium compounds into an alcohol capable of reducing the vanadium and contacting the mixture with alcohol modifying agents. The patent discloses two basic modes of calcination.: (1) air calcination and (2) nitrogen/steam calcination. In the air calcination the catalyst precursors are subjected to heating in air, as in one embodiment, to 400° C. over a two hours period, then holding at this temperature for six hours. In the nitrogen/steam calcination the catalyst precursors are first calcined in air, at a temperature in the range from 325° C. to 350° C. for six hours, followed by calcination in nitrogen and steam at a temperature in the range from 250° C. to 600° C. for from two to ten hours. The nitrogen/steam calcination is preferred.

U.S. Pat. No. 4,392,986 discloses a process for preparing vanadium-phosphorus catalysts by reaction in isobutanol followed by water washing of the precursors. The precursors, after drying at 120° C. to 140° C., are activated in the reactor oxidizing butane in air to maleic anhydride, typifying the in-situ calcination type.

U.S. Pat. No. 4,336,198 relates to vanadium-phosphorus catalysts modified with uranium, in which the precursors are supported on inert porous media such as alundum shapes. Calcining of the coated particles is disclosed as "heating from 200° C. to 400° C. at a rate of 5°/minute with heating at 400° C. for one hour".

U.S. Pat. No. 4,317,777 teaches the production of maleic anhydride using vanadium-phosphorus catalysts by oxidizing a mixture which comprises a hydrocarbon of at least 4 linear carbon atoms and an oxygen containing gas, which compositions are above the flammable limit. All of the catalysts described in the 18 examples were calcined as typified by the description: "The catalyst was calcined in-situ by heating to 385° C. at a rate of 9°/minute, whilst a 1.5% v/v n-butane/air mixture flowed through the bed at a GHSV of 1000 hr$^{-1}$". After several hundred hours of operation the performances of the catalysts were evaluated.

U.S. Pat. No. 4,315,864 teaches a process for preparing catalysts useful in the production of dicarboxylic acid anhydrides comprising the steps of:

a) introducing a pentavalent vanadium-containing compound into an olefinic, oxygenated organic liquid medium;

b) effecting reduction of at least a portion of said vanadium to a valence state of +4;

c) adding a phosphorus-containing compound to said medium to form a catalyst precursor precipitate;

d) recovering the catalyst precursor precipitate;

e) drying the catalyst precursor precipitate;

f) calcining the catalyst precursor precipitate.

The calcination procedure was typified by the description: "The catalyst precursor was then tableted with 1% graphite being added, in a Buechler press to 1⅛ inch. diameter. The tablets were then calcined in air from 150° C. to 400° C. at a rate of 5° C. per minute, being held at 400° C. for 1 hour".

These and many other references teach various methods of calcining the vanadium-phosphorus precursor to produce catalysts which in turn produce maleic anhydride with more or less efficiency. The prior art does not teach the benefit of a chemical pretreatment of the catalyst prior to its final activation by calcination, as described in the instant invention. Furthermore the prior art does not teach the benefit of combining such chemical pretreatment with a slow heat up rate above the temperature which will not substantially oxidize the residual organic materials arising from the organic media used, nor does the prior art teach that the slow heat up rate of preferred range of the instant invention, from about 150° C. to about to about 550° C., following the chemical pretreatment, produces catalysts improved in activity, productivity and yield. On the contrary, the procedures, in which rate of heating is mentioned, and/or programmed, teach increasing the temperature at 1° C./minute or higher.

As the only apparent exception, U.S. Pat. No. 5,847,163 mentions a heat up rate of from 0.1° C. per minute to about 10° C. per minute. Such a wide range of heat up rate is not associated with any chemical pretreatment, but only to the transformation of the precursor into an active catalyst in a fluidized bed.

Furthermore, U.S. Pat. No. 5,867,163 does not show any benefit of operating the calcination at heat up rates of less than 1° C. per minute, specifying, on the contrary the preferred heat up rate to be in the range from about 1° C. per minute to about 4° C. per minute (see column 4, lines 20–21).

All references cited by this specification are incorporated by reference in their entirety.

SUMMARY OF THE INVENTION

This invention is directed providing a process for the preparation of oxidation catalysts containing the mixed oxides of vanadium and phosphorus having improved activity and yield in the oxidation of 4-carbon hydrocarbons to maleic anhydride.

The above object is attained by the instant invention in a process entailing transformation of a precursor prepared using a non-aqueous solvent system, referred herein also as an organic solvent or an organic media, in the reduction, reaction and precipitation into vanadyl hydrogen phosphate precursor and its transformation into vanadyl pyrophosphate active catalyst, which process comprises:

a) contacting a phosphorus compound and vanadium compound in an organic solvent under conditions which will provide a catalyst precursor having a phosphorus to vanadium atom ratio between about 0.9 to 1.2 and having more than 90 atom percent of the vanadium in the tetravalent state;

b) recovering the precursor;

c) drying the precursor, limiting the maximum temperature in an oxygen-containing atmosphere, to a value which will not allow any substantial oxidation of the residual organic materials;

d) submitting the precursor, prior to calcination, to a chemical pretreatment by contacting with dry inert gas containing vapors of an aliphatic anhydride, having from 4 to 8 carbon atoms, preferably acetic anhydride, at a temperature not to exceed about 200° C.;

e) providing an atmosphere selected from the group consisting of air, steam, inert gases and mixtures thereof, and calcining the precursor, in said atmosphere, by raising the temperature, as measured in the precursor, above that attained in step (d) at a rate of less than 1° C. per minute to a temperature greater than 350° C., but no greater than 550° C., and maintaining the temperature for a time effective in giving a vanadium oxidation state no greater than +4.5 and in completing the conversion to generate an active catalyst.

DETAILED DESCRIPTION OF THE INVENTION

The process of this invention provides an added dimension of efficiency and reproducibility to the preparation of vanadyl pyrophosphate catalysts that use the non-aqueous solvent procedure for the making of the vanadium-phosphorus oxide precursor with or without modifying components. The catalysts, when made in accordance with the process of the present invention, give higher yields and activities than those made in accordance with previously taught technology (see U.S. Pat. No. 5,137,860), because the precursor, prior to calcination, is pretreated by contacting with dry inert gas containing vapors of aliphatic anhydride, preferably acetic anhydride, and because the rate of heating used during activation is less than 1° C. per minute.

The preparation of precursors using an organic solvent as the reaction medium is well known in the art. Specific examples of suitable catalyst precursors are described in several patents and publications, e.g., U.S. Pat. Nos. 4,632, 915, 4,562,268, 4,333,853, 4,315,864, 4,132,670, 4,064, 070; J. W. Johnson et al., J. Am. Chem. Soc., 106, 8123 (1984); F. Cavani et al. Appl. Catal., 9, 191 (1984); H. S.

Horowitz et al., Appl. Catal., 38, 193 (1988); R. S. K. Bej et al., Appl. Catal., 83, 149 (1992); R. Sant et al., J. Catal., 143, 215 (1993).

It is understood that the references are not to be construed as limiting, but are for purposes of illustration and guidance in the practice of the instant invention.

Broadly described, the precursor/catalysts of this invention are prepared by contacting a phosphorus compound and vanadium compound in an organic solvent under conditions which will provide a catalyst precursor having a phosphorus to vanadium atom ratio between about 0.9 to 1.2, and having greater than 90 atom percent of the vanadium in the tetravalent state. The catalyst precursors are recovered, dried, subjected to a chemical pretreatment by the action of an aliphatic anhydride and formed into structures for multi-tubular reactors, or sized for use in fluidized and transport reactors; or alternately, recovered, dried, pretreated and calcined before forming into structures or sizing. Thereafter these catalyst precursors are heat-treated by drying, subjected to chemical pretreatment, and heat-treated by calcining in accordance with the instant invention to obtain an active vanadyl pyrophosphate.

The vanadium compounds useful as source of vanadium in the catalyst precursors are well known in the art. Suitable vanadium compounds include but are not limited to: vanadium oxides, such as vanadium pentoxide, vanadium tetroxide and the like; vanadium oxyhalides, such as vanadyl chloride, vanadyl dichloride, vanadyl bromide, vanadyl dibromide and the like; vanadium salts, such as ammonium metavanadate, vanadyl sulfate, vanadyl phosphate, vanadyl formate, vanadyl oxalate and the like. Of these, however, vanadium pentoxide is preferred.

The phosphorus compounds also are well known in the art. Suitable phosphorus compounds include but are not limited to: phosphoric acids, such as ortho, meta phosphoric acids and the like; phosphorus oxides, such as phosphorus pentoxide and the like; phosphorus halides, such as phosphorus oxychloride, phosphorus oxybromide and the like; phosphorus in the trivalent state, such as phosphorus acid, phosphorus trichloride, organic phosphites and the like. Orthophosphoric acid and phosphorus pentoxide and mixtures thereof are preferred.

The organic liquid reaction medium may be used as a reducing agent for the vanadium, or an added agent may be used to reduce at least 90% of the vanadium to the +4 valence state upon addition of the vanadium or by heating.

In addition the liquid medium should be a solvent for the phosphorus compound and be relatively unreactive towards the phosphorus compound, while preferably not being a good solvent for the vanadium compound or for the vanadium-phosphorus oxide precursor. Suitable liquid media for use in the invention are organic compounds such as alcohols, aldehydes, ketones, ethers and mixtures of the above. The use as a solvent of an anhydride, such as acetic anhydride, has been investigated (see U.S. Pat. No. 3,864,280), but found to be unsuitable leading to catalysts with very poor performances of conversion and yield. The organic liquid media used are usually substantially anhydrous. A preferred organic liquid consists of a mixture of anhydrous isobutanol and benzyl alcohol.

It is apparent to those skilled in the art that the catalyst precursor materials, once separated from the reaction media and dried, may be formed into suitably shaped structures for use in a maleic anhydride reactor. Techniques for configuring precursor powder for use as catalysts in fixed-bed, heat exchanger type reactors, fluidized-bed reactors and transport-bed reactors are well known to those skilled in the art. For example, the catalyst precursors may be tableted or extruded for use in a fixed-bed reactor or transport-bed reactor.

The precursor may be supported on suitable carrier for use in any of the reactors. Representative carriers include, but are not limited to, silica, alumina, silicon carbide, silica-alumina and titanium dioxide.

Minor amounts of metals, in the form of oxides or phosphates, are often included in vanadyl phosphate catalysts as promoters. Other modifiers may be added in some instances to change catalyst performances.

In the present invention the catalyst precursor is converted to the active catalyst through limiting the maximum temperature of the drying step in oxygen containing atmosphere, pretreating by contact with vapors of an aliphatic anhydride, preferably acetic anhydride, in dry inert gas at a temperature not to exceed about 200° C., and limiting the rate of temperature increase in the calcination step. The pretreatment of the precursor with inert gas containing vapors of an aliphatic anhydride is the most relevant embodiment of this invention, having a very positive role in the production of an active catalyst with superior performances in the production of maleic anhydride by oxidation of aliphatic hydrocarbons. The pretreating-activation-conversion steps are also critical to the preparation of the superior catalysts attendant with the instant invention. The invention accomplishes the critical pretreating activation-conversion steps also by limiting the temperature during the drying and pretreating steps and the rate of heating and the atmosphere in contact with the catalyst during the calcination step.

In the drying and pretreating step the maximum temperature is limited to a value which will not allow the oxidation of the residual organic materials arising from the organic media used. A preferable maximum temperature range is from about 150° C. to 200° C.

In the drying step the volatile organic materials arising from the organic media used are removed with less than 50° C. over-temperature (hot-spots) in the precursor, avoiding a rapid oxidation of the residual organic materials.

In the activation-conversion (calcination) step the transformation is carried out by raising the temperature in a suitable atmosphere at a rate of less than 1° C. per minute, minimizing the over-temperature (hot-spots) in the catalyst.

Prior technology teaches that the activation-conversion stage (calcination) begins at a substantially higher temperature than 150° C. to 200° C. However, remarkably, it has been discovered that, as opposed to prior teachings, a fast rate of heating above 150° C. to 200° C. adversely affects, in a significant manner, the performance of the resulting active catalyst.

Several sources teach the use of steam, oxygen and inert gas, the last two usually supplied by air, during the calcination of the precursor. It is well known that the steam is needed to gain the highest performances of the active catalysts. Also, it is well known in the art that the temperature, oxygen concentration, and time variables may be used to control the partial re-oxidation of the vanadium in the catalyst. In the instant invention the atmosphere concentrations of steam, inert gas and oxygen is controlled to provide a vanadium oxidation state above 4.0 to about 4.5, preferably from 4.05 to 4.2. In the preferred embodiment of the instant invention a single mixture of steam, inert gas and oxygen may be used, thus significantly simplifying the activation-conversion of the precursor to a commercially feasible procedure.

For the purpose of comparing the performance efficiencies of catalysts made pursuant with the instant invention with comparative technologies, the active catalyst forms may be tested using a variety of reactor types which are well known in the art. As in the instant invention the comparison is made by actually reacting a hydrocarbon, usually n-butane, as an admixture with air on a sample of catalyst in a single tube reactor. The measured performance variables include temperature of the heat exchange media of the reactor, conversion (usually one-pass conversion) of the feed hydrocarbon, yield of maleic anhydride based on the feed hydrocarbon.

Activity may be expressed by the level of conversion attained at a given temperature in the medium surrounding the reactor. In the instant development the conversion of the butane feed at 400° C. is used. The conversion at 400° C. "bath" temperature may typically be from about 60% to 85% of the hydrocarbon feed, but often is lower or higher, the level of conversion reflecting the activity of the catalyst.

The yield of maleic anhydride is expressed as the moles of maleic anhydride produced from 100 moles of butane fed to the reactor. The commercial value of a catalyst may be judged by the two variables, yield and conversion. The yield is a direct measure of the raw material usage, while conversion at a given temperature is a direct measure of activity. Mathematically, the ratio of the yield and conversion is the selectivity, which is usually expressed as the moles of maleic anhydride formed per 100 moles of hydrocarbon reacted and is a measure of the chemical efficiency. Combined with high conversion, high selectivities portend the capability of attaining high yields and consequently low raw material usage.

In the comparative testing of the instant development, a volume of 50 ml of the catalyst is charged to a 21 mm diameter stainless steel reactor to an approximate depth of 180 mm and the reactor submerged in a liquid-mixed salt bath. The salt bath used is a mixture of potassium nitrate, sodium nitrate and sodium nitrite, the eutectic being the most commonly commercially used heat transfer medium.

Comparative testing have been performed, described as follows, in once through operating conditions of reaction using air as oxidizing medium and in operating conditions of off-gas recycling using oxygen as oxidizing medium.

EXAMPLE 1

This example illustrates a suitable procedure for preparation of a standard catalyst precursor form.

A 10-liter, four-neck, round-bottom flask, fitted with a mechanical stirrer with a 15 cm TEFLON paddle, a thermometer, a heating mantle, and a reflux condenser, was charged with 6480 ml (5196 g) of isobutyl alcohol and 720 ml (750 g) of benzyl alcohol. Stirring was started (about 350 r.p.m.) and 670 g (3.7 moles) of vanadium pentoxide ($V_2O_5$) was added. The mixture was heated to reflux, about 107° C., and maintained at reflux for 3 hours. After the initial reflux period the stirred mixture is cooled to about 20° C. below the reflux temperature and 816 g (8.3 moles) of freshly prepared phosphoric acid (106% $H_3PO_4$) was added. The resultant mixture was again heated to reflux and maintained at reflux for 16 hours. This mixture was cooled to about 50° C. and suction filtered to yield a bright blue cake. The blue solid was transferred to four open 2-liter dish trays and dried in a forced-draft oven at 150° C. for 10 hours to yield about 1300 g of a grey-blue catalyst precursor powder.

The resultant powder, thus prepared, was chemically pretreated as described in Example 2.

As alternative, the resultant powder was passed with some pressing through a 65-mesh sieve, blended with approximately 4% by weight graphite, and 4 mm×4 mm cylindrical tablets were formed in a Stokes-512 tableting machine equipped with one die. The catalyst precursor tablets, thus prepared, were calcined under varying conditions as described in Example 3.

EXAMPLE 2

This example illustrates a suitable procedure for the preparation of a catalyst precursor form according to the chemical pretreatment procedure, one of the embodiments of the instant invention.

A 100 ml portion of the grey-blue catalyst precursor powder of Example 1 were charged to a 50 mm diameter borosilicate tube and placed in a vertical Lindberg oven.

Before starting the chemical pretreating program, dry inert gas (160 L/hr) was passed through the catalyst bed to remove residual oxygen in the atmosphere in contact with the catalyst.

Then the temperature of the precursor was controlled at about 150° C., while acetic anhydride vapors were gradually injected into the inert gas stream at a molar concentration variable from 1 to 20%, preferably from 2 to 5% by volume. The pretreatment was continued for about 8 hours. At the end of the pretreatment the residual acetic anhydride in the atmosphere was removed by a flow of nitrogen.

The resultant powder was passed with some pressing through a 65 mesh sieve, blended with approximately 4% by weight graphite, and 4 mm×4 mm cylindrical tables were formed in a Stokes-512 tabletting machine equipped with one die. The catalyst precursor tablets, thus prepared, were calcined under varying conditions as described in Example 3.

EXAMPLE 3

This example describes the procedure employed to compare standard methods of calcination with the calcination procedure embodied in the instant invention.

Portions of 100 ml each of the catalyst precursor tablets of Example 1 and of Example 2 were charged to a 50 mm diameter borosilicate tube and placed in a vertical Lindberg oven.

Before starting the heating program, dry inert gas (160 L/hr) was passed through the catalyst bed. When the temperature of the tablets reached 150° C., the temperature was increased at programmed rates, as indicated in TABLES 1, 2 and 3, to 420° C. and held constant at 420° C. for 8 hr.

At the end of the heating program, the atmosphere was replaced by a flow of nitrogen and the calcined tablets were cooled.

PERFORMANCE TESTS

The prepared catalysts were tested for performance as described heretofore.

The catalysts are identified as follows:

Type A=standard catalyst prepared according Example 1, with rate of temperature rise in calcination of 2° C. or higher.

Type B=catalyst subjected to chemical pretreatment, according one of the embodiments of the instant invention, as described in Example 2, with a rate of temperature rise in calcination of 2° C. or higher.

Type C=catalyst subjected to chemical pretreatment, according one of the embodiments of the instant invention, as described in Example 2, with a rate of temperature rise in calcination of less than 2° C.

TABLE 1 lists the performance results of a standard once through butane oxidation using air as oxidizing medium.

All the tests summarized in TABLE 1 were performed in identical operating conditions of reaction, that means:

Oxidizing medium: air
Butane concentration in the feed: 1.5% vol.
GHSV: 1400 hr$^{-1}$
Salt bath temperature: 400° C.

TABLE 1

| | Heating rate (° C./min) | Yield % | Conversion % | Selectivity % |
|---|---|---|---|---|
| TYPE A CATALYST | | | | |
| A-1 | 2 | 68 | 66 | 45 |
| A-2 | 4 | 54 | 68 | 37 |
| A-3 | 15 | 50 | 68 | 34 |
| TYPE B CATALYST | | | | |
| B-1 | 2 | 78 | 67 | 52 |
| B-2 | 4 | 72 | 68 | 49 |
| B-3 | 15 | 62 | 68 | 42 |
| TYPE C CATALYST | | | | |
| C-1 | 0.5 | 85 | 67 | 57 |
| C-2 | 1.0 | 82 | 68 | 56 |
| CA-3 | 1.5 | 78 | 69 | 54 |

TABLE 2 lists the performance results of a butane oxidation using as oxidizing medium oxygen diluted in recycling off gases.

All the tests summarized in TABLE 2 were performed under the following identical reaction conditions.

Oxidizing medium: oxygen in recycling off gases
Oxygen concentration in feed: 12.3% vol.
Butane concentration in feed: 5.6% vol.
GHSV: 2500 hr$^{-1}$
Salt bath temperature: 400° C.

TABLE 2

| | Heating rate (° C./min) | Conversion per Pass % | Global Conversion % | Selectivity % | Yield % |
|---|---|---|---|---|---|
| TYPE A CATALYST | | | | | |
| A-1 | 2 | 39 | 95 | 64 | 61 |
| A-2 | 4 | 39 | 94 | 62 | 58 |
| A-3 | 15 | 38 | 94 | 55 | 52 |

| | Heating rate (° C./min) | Conversion % | Global Conversion % | Selectivity % | Yield % |
|---|---|---|---|---|---|
| TYPE B CATALYST | | | | | |
| B-1 | 2 | 39 | 96 | 73 | 70 |
| B-2 | 4 | 38 | 95 | 70 | 67 |
| B-3 | 15 | 38 | 94 | 67 | 63 |
| TYPE C CATALYST | | | | | |
| C-1 | 0.5 | 38 | 97 | 75 | 73 |
| C-2 | 1.0 | 37 | 96 | 75 | 72 |
| C-3 | 1.5 | 37 | 96 | 74 | 71 |

Comparisons of yields in TABLE 1 and TABLE 2 shows that both the treatment step of the precursor and the low rate of temperature increase in calcination, as taught in the instant invention, allow significantly better yields than the comparative catalysts of TYPE A.

The comparison shows also that the catalyst prepared according the procedures of this invention are particularly suited for the production of maleic anhydride by a gas recycle process.

A suitable gas recycle process is a process ior the production of maleic anhydride by the oxidation of n-butane with molecular oxygen or a molecular oxygen containing gas in the vapor phase at a temperature of about 300° C. to 550° C. in the presence of a phosphorus-vanadium mixed oxide catalyst made according to the embodiments of this invention, where the reaction feed mixture consists of pure oxygen, butane and a recycle gaseous stream being regulated so that the oxygen concentration in the reaction mixture ranges from 5 to 16% by volume, the butane concentration in the reaction mixture ranges from 2 to 20% by volume, and where said reaction mixture is feed to an oxidation reactor where a phosphorus-vanadium mixed oxide catalyst made according to the embodiments of this invention causes butane to react at moderate conversion per pass producing maleic anhydride with high yield.

It is understood that the invention is not limited to the above embodiments and that many changes may be made without departing from the spirit of the invention.

What is claimed is:

1. A process for the preparation of oxidation catalysts containing mixed oxides of vanadium and phosphorus, to be used for the production of maleic anhydride by oxidation of aliphatic hydrocarbons in a fixed bed reactor, which comprises the steps of:
   a) contacting a phosphorus compound and a vanadium compound in an organic solvent under conditions which will provide a catalyst precursor having a phosphorus to vanadium atom ratio between about 0.9 to 1.2 and having more than 90 atom percent of the vanadium in the tetravalent state;
   b) recovering the precursor;
   c) drying the precursor, limiting the maximum temperature, in an oxygen containing atmosphere, to a value which will not substantially oxidize the residual organic materials arising from the organic solvent used;
   d) submitting the precursor, prior to calcination, to a chemical pretreatment by contacting with dry inert gas containing vapors of an aliphatic anhydride selected from the group consisting of acetic anhydride, propionic anhydride and butyric anhydride, at a temperature not exceeding 200° C.,
   e) providing an atmosphere selected from the group consisting of air, steam, inert gases and mixtures thereof, and calcining the precursor in said atmosphere, by raising the temperature, as measured in the precursor, above that attained in step (d) at a rate of less than 1° C. per minute to a temperature greater than 350° C., but no greater than 550° C. and maintaining the temperature for a time effective in giving a vanadium oxidation state no greater than +4.5 and in completing the conversion to generate an active catalyst.

2. The process of claim 1, wherein the maximum temperature of drying in Step (c) is lower than 250° C. in an oxygen containing atmosphere.

3. The process of claim 1, wherein the maximum temperature of drying in Step (c) is about 150° C. to 200° C. in an oxygen containing atmosphere.

4. The process of claim 1, wherein the rate of temperature increase in Step (e) is less than 1° C./minute.

5. The process of claim 1, wherein the pretreating agent in Step (d) is an aliphatic anhydride selected from the group consisting of propionic anhydride and butyric anhydride.

6. The process of claim 1, wherein the proportion of aliphatic anhydride in inert gas in the pretreatment Step (d) is within 1% to 20% by volume.

7. The process of claim 1, wherein the temperature of the precursor, in the pretreatment Step (d) does not exceed 200° C.

8. The process of claim 1, wherein the temperature of the precursor is increased in Step (e) from about 350° C. to about 450° C.

9. The process of claim 1, wherein the gas atmosphere in Step (c) contains a proportion of oxygen greater than 0 percent by volume but no greater than about 15 percent by volume.

10. The process of claim 1, wherein the gas atmosphere in Step (e) contains a proportion of oxygen greater than 0 percent by volume but no greater than about 15 percent by volume.

11. The process of claim 1, wherein the gas atmosphere in Step (e) contains a proportion of steam greater than 0 percent by volume but no greater than about 75 percent by volume.

12. The process of claim 1, wherein the recovered precursor in Step (d) is formed into structures for multi-tubular reactors.

13. The process of claim 1, wherein the recovered precursor in Step (d) is calcined before forming into structures for multi-tubular reactors.

14. A phosphorous-vanadium mixed oxide hydrocarbon oxidation catalyst, to be used for the production of maleic anhydride by oxidation of aliphatic hydrocarbons in a fixed bed reactor, made by a process comprising the steps of:
   a) contacting a phosphorus compound and a vanadium compound in an organic solvent under conditions which will provide a catalyst precursor having a phosphorus to vanadium atom ratio between about 0.9 to 1.2 and having more than 90 atom percent of the vanadium in the tetravalent state;
   b) recovering the precursor;
   c) drying the precursor, limiting the maximum temperature, in an oxygen containing atmosphere, to a value which will not substantially oxidize the residual organic materials arising from the organic solvent used;
   d) submitting the precursor, prior to calcination, to a chemical pretreatment by contacting with dry inert gas containing vapors of an aliphatic anhydride atoms, selected from the group consisting of acetic anhydride, propionic anhydride and butyric anhydride, at a temperature not exceeding 200° C.,
   e) providing an atmosphere selected from the group consisting of air, steam, inert gases and mixtures thereof, and calcining the precursor in said atmosphere, by raising the temperature, as measured in the precursor, above that attained in step (d) at a rate of less than 1° C. per minute to a temperature greater than 350° C., but no greater than 550° C. and maintaining the temperature for a time effective in giving a vanadium oxidation state no greater than +4.5 and in completing the conversion to generate an active catalyst.

15. The process of claim 1, wherein the rate of temperature increase in Step (e) is about 0.5° C./minute.

16. The process of claim 1, wherein the pretreating agent in Step (d) is acetic anhydride.

17. The process of claim 1, wherein the proportion of aliphatic anhydride in inert gas in the pretreatment Step (d) is from 2% to 5% by volume.

18. The process of claim 1, wherein the temperature of the precursor, in the pretreatment Step (d) is from 130 to 160° C.

19. The process of claim 1, wherein the temperature of the precursor is increased in Step (e) from about 375° C. to about 430° C.

20. The process of claim 1, wherein the gas atmosphere in Step (c) contains a proportion of oxygen from about 4 percent by volume to about 8 percent by volume.

21. The process of claim 1, wherein the gas atmosphere in Step (e) contains a proportion of oxygen from about 4 percent by volume to about 8 percent by volume.

22. The process of claim 1, wherein the gas atmosphere in Step (e) contains a proportion of steam from about 30 percent by volume to about 60 percent by volume.

23. The process of claim 1, wherein the catalyst is to be used for the production of maleic anhydride by oxidation of n-butane in a fixed bed reactor.

24. The process of claim 1, wherein the pretreating agent in Step (d) comprises acetic anhydride.

25. The catalyst of claim 14, wherein the maximum temperature of drying in Step (c) is lower than 250° C. in an oxygen containing atmosphere.

26. The catalyst of claim 14, wherein the rate of temperature increase in Step (e) is less than 1° C./minute.

27. The catalyst of claim 14, wherein the pretreating agent in Step (d) is an aliphatic anhydride selected from the group consisting of acetic anhydride.

28. The catalyst of claim 14, wherein the temperature of the precursor, in the pretreatment Step (d) does not exceed 200° C.

29. The catalyst of claim 14, wherein the gas atmosphere in Step (c) contains a proportion of oxygen greater than 0 percent by volume but no greater than about 15 percent by volume.

30. The catalyst of claim 14, wherein the gas atmosphere in Step (e) contains a proportion of steam greater than 0 percent by volume but no greater than about 75 percent by volume.

31. The catalyst of claim 14, wherein the recovered precursor in Step (d) is formed into structures for multi-tubular reactors.

* * * * *

UNITED STATES PATENT AND TRADEMARK OFFICE
CERTIFICATE OF CORRECTION

PATENT NO.    : 6,174,833 B1           Page 1 of 1
DATED         : January 16, 2001
INVENTOR(S)   : Bertola et al.

It is certified that error appears in the above-identified patent and that said Letters Patent is hereby corrected as shown below:

Column 3,
Line 62, U.S. Patent No. -- 5,847,163 -- instead of "5,867,163";

Column 9,
Table 1, after "(°C/min)", change "Yield" to -- Selectivity --; after "Conversion %", change "Selectivity" to -- Yield --.

Signed and Sealed this

Fifth Day of March, 2002

Attest:

Attesting Officer

JAMES E. ROGAN
*Director of the United States Patent and Trademark Office*